(12) United States Patent
Lautensack et al.

(10) Patent No.: US 8,067,618 B2
(45) Date of Patent: Nov. 29, 2011

(54) METHOD FOR GAS PHASE OXIDATION USING A MODERATOR LAYER

(75) Inventors: Thomas Lautensack, Birkenau (DE); Hans-Martin Allmann, Neunkirchen (DE); Hagen Wilmer, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 614 days.

(21) Appl. No.: 12/298,453

(22) PCT Filed: Apr. 27, 2007

(86) PCT No.: PCT/EP2007/054150
§ 371 (c)(1),
(2), (4) Date: Oct. 24, 2008

(87) PCT Pub. No.: WO2007/125096
PCT Pub. Date: Nov. 8, 2007

(65) Prior Publication Data
US 2009/0171101 A1   Jul. 2, 2009

(30) Foreign Application Priority Data

Apr. 27, 2006 (EP) .................... 06008816

(51) Int. Cl.
*C07D 307/89* (2006.01)
(52) U.S. Cl. ...................................... 549/248
(58) Field of Classification Search .................. 549/248
See application file for complete search history.

(56) References Cited

U.S. PATENT DOCUMENTS

| | | | |
|---|---|---|---|
| 5,225,574 | A | 7/1993 | Aichinger et al. |
| 6,700,000 | B1 | 3/2004 | Heidemann et al. |
| 2008/0194844 | A1 | 8/2008 | Guckel et al. |

FOREIGN PATENT DOCUMENTS

| | | |
|---|---|---|
| DE | 4013051 A1 | 11/1991 |
| DE | 19823262 A1 | 12/1999 |
| EP | 0326536 A1 | 8/1989 |
| EP | 1063222 A1 | 12/2000 |
| WO | WO-2005/063673 | 7/2005 |
| WO | WO-2005/063673 A1 | 7/2005 |
| WO | WO-2006/092305 | 9/2006 |
| WO | WO-2008/022909 | 2/2008 |
| WO | WO-2008/022911 | 2/2008 |
| WO | WO-2009/021924 | 2/2009 |
| WO | WO-2009/124947 | 10/2009 |

OTHER PUBLICATIONS

U.S. Appl. No. 12/015,741, filed Jan. 17, 2008, Raichle, et al.
U.S. Appl. No. 12/039,231, filed Feb. 28, 2008, Cremer, et al.
U.S. Appl. No. 12/138,862, filed Jun. 13, 2008, Cremer, et al.
U.S. Appl. No. 12/138,823, filed Jun. 13, 2008, Raichle, et al.
U.S. Appl. No. 12/297,895, filed Oct. 21, 2008, Mauer, et al.
U.S. Appl. No. 12/301,352, filed Nov. 18, 2008, Mackewitz, et al.
U.S. Appl. No. 12/301,370, filed Nov. 18, 2008, Mackewitz, et al.
U.S. Appl. No. 12/301,420, filed Nov. 18, 2008, Wilmer, et al.
U.S. Appl. No. 12/305,698, filed Dec. 19, 2008, Wilmer, et al.
U.S. Appl. No. 12/520,648, filed Jun. 22, 2009, Wilmer, et al.
U.S. Appl. No. 12/936,807, filed Oct. 7, 2010, Wilmer, et al.
International Preliminary Report on Patentability issued on Jan. 15, 2009 in corresponding International Application No. PCT/EP2007/054150.

*Primary Examiner* — Bernard Dentz
(74) *Attorney, Agent, or Firm* — Connolly Bove Lodge & Hutz LLP

(57) ABSTRACT

A process for gas phase oxidation in which a gaseous stream which comprises at least one aromatic hydrocarbon and molecular oxygen is passed through one or more catalyst layers, wherein a moderator layer is arranged between two catalyst layers arranged in succession in flow direction of the gaseous stream, the moderator layer being less catalytically active than the catalysts adjacent upstream and downstream or being catalytically inactive. The desired oxidation products are obtained in high yield over prolonged periods.

20 Claims, 2 Drawing Sheets

METHOD FOR GAS PHASE OXIDATION USING A MODERATOR LAYER

CROSS REFERENCE TO RELATED APPLICATIONS

This application is a 35 U.S.C. 371 National Stage Application of International Application No. PCT/EP2007/054150, filed Apr. 27, 2007, which claims priority from European Application No. 06008816.8, filed Apr. 27, 2006, the entire contents of both applications are incorporated herein by reference in their entireties.

The present invention relates to a process for gas phase oxidation in which a gaseous stream which comprises an aromatic hydrocarbon and molecular oxygen is passed through two or more catalyst layers.

A multitude of carboxylic acids and/or carboxylic anhydrides is prepared industrially by the catalytic gas phase oxidation of aromatic hydrocarbons such as benzene, the xylenes, naphthalene, toluene or durene in fixed bed reactors. In this way, it is possible to obtain, for example, benzoic acid, maleic anhydride, phthalic anhydride, isophthalic acid, terephthalic acid or pyromellitic anhydride. In general, a mixture of an oxygenous gas and the starting material to be oxidized is passed through tubes in which a bed of a catalyst is present. For temperature control, the tubes are surrounded by a heat carrier medium, for example a salt melt.

Even though the excess heat of reaction is removed by the heat carrier medium, local temperature maxima (hotspots) can form in the catalyst bed, in which there is a higher temperature than in the remaining part of the catalyst bed. These hotspots lead to side reactions, such as the total combustion of the starting material, or to the formation of undesired by-products which can be removed from the reaction product only with a high degree of difficulty, if at all.

Moreover, the catalyst can be damaged irreversibly from a certain hotspot temperature. When the process is started up, the loading of the gaseous stream with the hydrocarbon to be oxidized has to be kept very low at first and can be increased only slowly. The final production state is often attained only after a few weeks.

To attenuate these hotspots, various measures have been taken. In particular, as described in DE-A 40 13 051, there has been a transition to the arrangement of catalysts of different activity layer by layer in the catalyst bed, the less active catalyst generally being placed toward the gas inlet and the more active catalyst toward the gas outlet.

DE 198 23 262 describes a process for preparing phthalic anhydride with at least three coated catalysts arranged one on top of another in layers, the catalyst activity rising from layer to layer from the gas inlet side to the gas outlet side.

EP-A 1 063 222 describes a process for preparing phthalic anhydride, which is performed in one or more fixed bed reactors. The catalyst beds in the reactors have three or more than three individual catalyst layers in succession in the reactor. After passing through the first catalyst layer, from 30 to 70% by weight of the o-xylene, naphthalene or the mixture of the two used has been converted under the reaction conditions. After the second layer, 70% by weight or more has been converted.

EP 326 536 describes a process for preparing maleic anhydride by gas phase oxidation of suitable nonaromatic hydrocarbon over a phosphorus-vanadium mixed oxide catalyst. Mixing of the catalyst with an inert solid material reduces the yield decrease per month in long-term operation.

WO 2005/063673 describes a process for preparing unsaturated aldehydes and/or carboxylic acids by partial oxidation over a fixed catalyst bed, a layer of inactive material being inserted at the point in the reaction zone at which the position of the hotspot is expected. The catalyst arranged downstream and upstream of the inactive material layer is identical.

The activity of the catalysts or catalyst systems used for the gas phase oxidation decreases with increasing operating time. A high proportion of unconverted hydrocarbons or partly oxidized intermediates gets into regions of the catalyst bed further downstream. The reaction shifts increasingly toward the reactor outlet and the hotspot migrates downstream. The catalyst deactivation can be counteracted to a limited degree by increasing the temperature of the heat carrier medium. The increase in the temperature of the heat carrier medium and/or the shifting of the hotspot lead, in multilayer catalyst systems, to a rise in the temperature with which the gas mixture enters a downstream catalyst layer. Since downstream catalyst layers are generally more active but less selective, undesired overoxidation and other side reactions increase. Overall, the product yield and selectivity fall with operating time.

It is an object of the invention to provide a process which permits the desired oxidation products to be obtained in high yield over prolonged periods.

The object is achieved by a process for gas phase oxidation in which a gaseous stream which comprises at least one aromatic hydrocarbon and molecular oxygen is passed through at least two catalyst layers arranged in succession in flow direction of the gaseous stream, the activity of the catalysts in adjacent catalyst layers being different from one another, wherein a moderator layer is arranged between two catalyst layers arranged in succession in flow direction of the gaseous stream, the moderator layer being less catalytically active than the catalysts adjacent upstream and downstream or being catalytically inactive and the catalyst layer downstream of the moderator layer has a higher activity than the catalyst layer upstream of the moderator layer.

In the present context, a catalyst layer refers to the bed of a catalyst with essentially uniform activity, i.e. with essentially uniform composition of the active composition, active composition fraction and packing density (disregarding unavoidable fluctuations in the filling of the reactor). Successive catalyst layers thus differ in the activity of the catalysts present. The person skilled in the art is familiar with various measures for controlling the catalyst activity, as detailed below. Within a catalyst layer, the catalyst particles are not diluted by particles of an inert material.

Activity of a catalyst or of a catalyst layer is understood to mean the conversion which is measured in a test plant under identical conditions (especially with regard to catalyst volume, volume-based superficial velocity (gas hourly space velocity, GHSV) and air rate, temperature of the heat carrier medium, hydrocarbon loading of the gaseous stream). The higher the conversion of a catalyst or of a catalyst layer, the higher its activity. This method is suitable in particular for comparing activities and for determining relative catalyst activities.

The invention envisages one or more moderator layers which are arranged between two catalyst beds such that they are passed through by the gaseous stream which leaves the upstream catalyst bed before it enters the downstream catalyst bed.

The moderator layer consists appropriately of a bed of a particulate material. With regard to easy filling of the reactor and a uniform pressure drop, the particulate material appropriately has similar dimensions to the catalyst particles.

The moderator layer may be catalytically inactive. In this case, it consists of an inert material, as, for example, also used as a catalyst support. Suitable support materials are, for example, quartz (SiO$_2$), porcelain, magnesium oxide, tin dioxide, silicon carbide, rutile, alumina (Al$_2$O$_3$), aluminum silicate, steatite (magnesium silicate), zirconium silicate, cerium silicate, or mixtures of these support materials. The moderator layer may also comprise wovens, loop-drawn knits or loop-formed knits composed of fibers or metal wires.

The moderator layer may also have catalytic activity. In this case, the moderator layer is both less catalytically active than the upstream catalyst bed and less catalytically active than the downstream catalyst bed. This can be achieved by virtue of a high content of deactivating additives, low active composition fraction, dilution of a catalyst with inert material and/or other measures which are familiar to those skilled in the art. The contribution of a catalytically active moderator layer to the total conversion in the reactor is preferably small and is, for example, less than 10%, in particular less than 5%, of the total conversion. The contribution to the moderator layer is considered to be the amount of the aromatic hydrocarbon converted in the moderator layer, relative to the total amount of aromatic hydrocarbon converted in the reactor.

The moderator layer is arranged between two successive catalyst layers, the upstream catalyst bed and the downstream catalyst bed having different activity. In this case, the catalyst bed downstream of the moderator layer has a higher activity than the catalyst bed upstream of the moderator layer. The ratio of the volume of the moderator layer to the volume of the catalyst layer upstream of the moderator layer is preferably from 0.05 to 0.35, in particular from 0.1 to 0.25.

The proportion of the volume of the moderator layers in the total volume of catalyst and moderator layers is generally not more than 40%.

In preferred embodiments, the gaseous stream is passed through at least three catalyst layers arranged in succession in flow direction of the gaseous stream, for example through three, four or five catalyst layers. In embodiments having three catalyst layers, a moderator layer is preferably arranged between the second and third catalyst layer. In embodiments having four catalyst layers, a moderator layer is preferably arranged between the second and third catalyst layer and/or between the third and fourth catalyst layer.

When a plurality of catalyst layers are used, various configurations of the activity graduation are possible. In a preferred embodiment, the activity of the catalysts in flow direction of the gaseous stream increases constantly from one catalyst layer to the next from the catalyst layer closest to the gas inlet to the catalyst layer closest to the gas outlet. A moderator layer is preferably arranged at least between the penultimate and last catalyst layer in flow direction.

In another preferred embodiment, the gaseous stream is passed through more than three catalyst layers arranged in succession in flow direction of the gaseous stream; in this case, the activity of the catalysts increases from one catalyst layer to the next over a sequence of at least three of the catalyst layers in flow direction of the gaseous stream. Thus, it is possible to provide a relatively short, highly active catalyst layer as the furthest upstream catalyst layer, which is followed downstream by a less active catalyst layer, and this less active catalyst layer may be followed by further layers with activity rising stepwise.

The moderator layer(s) provided in accordance with the invention bring(s) about a cooling of the gaseous stream before it enters the bed of the catalyst arranged downstream of the moderator layer. The cooling is evident from the temperature profile, i.e. a plot of the temperature as a function of the catalyst bed length. The temperature profile can be determined easily by means of thermoelements which are arranged in thermal tubes at different heights, for example equidistantly, or with a height-adjustable thermoelement.

The temperature at the downstream border of a moderator layer is preferably at least 2 K, in particular at least 4 K, lower than the temperature profile extrapolated from the catalyst upstream of the moderator layer. The extrapolated temperature profile can be calculated by the equation $$(\delta T \cdot x)$$

wherein $\delta T$ is the gradient of the temperature profile at the border of the catalyst upstream of the moderator layer from the moderator layer, and x is the length of the moderator layer in flow direction. The gradient of the temperature profile can be determined by placing a tangent onto the temperature profile at the border of the catalyst upstream of the moderator layer.

The temperature drop over the moderator layer is preferably at least 4 K, in particular at least 6 K and more preferably at least 8 K. The temperature drop is considered here to be the difference, determinable from the temperature profile, between the temperature at the upstream and the downstream border of the moderator layer.

It is preferred when the temperature of at least the moderator layer and the catalyst layers adjacent to it upstream and downstream can be controlled together, i.e. the reaction tubes in the region of the moderator layer and of the catalyst layers adjacent upstream and downstream are surrounded by a single heat transfer medium, for example a salt bath. The process is thus suitable particularly for reactors with only one heat transfer medium circuit.

The process according to the invention is suitable particularly for the gas phase oxidation of aromatic $C_6$- to $C_{10}$- hydrocarbons, such as benzene, the xylenes, toluene, naphthalene or durene (1,2,4,5-tetramethylbenzene) to carboxylic acids and/or carboxylic anhydrides such as maleic anhydride, phthalic anhydride, benzoic acid and/or pyromellitic dianhydride. The process is particularly suitable for preparing phthalic anhydride from o-xylene and/or naphthalene.

The catalytically active composition of all catalysts preferably comprises at least vanadium oxide and titanium dioxide. Measures for controlling the activity of gas phase oxidation catalysts based on vanadium oxide and titanium dioxide are known per se to those skilled in the art.

For instance, the catalytically active composition may comprise compounds which, as promoters, influence the activity and selectivity of the catalyst.

Examples of activity-and selectivity-influencing factors include alkali metal compounds, especially cesium oxide, lithium oxide, potassium oxide, sodium oxide and rubidium oxide, and phosphorus or sulfur compounds.

A further means of controlling the activity consists in varying the proportion of the active composition or of the $V_2O_5$ content in the total weight of the catalyst, higher active composition or $V_2O_5$ contents causing a higher activity and vice versa.

The catalysts used in the process according to the invention are generally coated catalysts in which the catalytically active composition is applied in coating form on an inert support. The layer thickness of the catalytically active composition is generally from 0.02 to 0.2 mm, preferably from 0.05 to 0.1 mm. In general, the catalysts have an active composition layer applied in coating form on an inert support.

The inert support materials used may be virtually all prior art support materials, as used advantageously in the preparation of coated catalysts for the oxidation of aromatic hydrocarbons to aldehydes, carboxylic acids and/or carboxylic anhydrides, for example quartz (SiO$_2$), porcelain, magnesium oxide, tin dioxide, silicon carbide, rutile, alumina ($Al_2O_3$), aluminum silicate, steatite (magnesium silicate), zirconium silicate, cerium silicate, or mixtures of these support materials. The support material is generally nonporous. Advantageous support materials which should be emphasized are in particular steatite and silicon carbide. The shape of the support material is generally not critical for the inventive precatalysts and coated catalysts. For example, catalyst supports in the form of spheres, rings, tablets, spirals, tubes, extrudates or spall may be used. The dimensions of these catalyst supports correspond to those catalyst supports typically used for the preparation of coated catalysts for the gas phase partial oxidation of aromatic hydrocarbons. Preference is given to using steatite in the form of spheres having a diameter of from 3 to 6 mm, or of rings having an external diameter of from 5 to 9 mm and a length of from 4 to 7 mm.

The individual layers of the coated catalyst can be applied by any methods known per se, for example by spray application of solutions or suspensions in a coating drum, or coating with a solution or suspension in a fluidized bed. It is possible to add organic binders, preferably copolymers, advantageously in the form of an aqueous dispersion, of vinyl acetate/vinyl laurate, vinyl acetate/acrylate, styrene/acrylate, vinyl acetate/maleate, vinyl acetate/ethylene and hydroxyethylcellulose, to the catalytically active composition, amounts of binders of from 3 to 20% by weight, based on the solids content of the solution of the active composition constituents, being used advantageously. When the catalytically active composition is applied to the support without organic binder, coating temperatures above 150° C. are advantageous. When the abovementioned binders are added, the useable coating temperatures, depending on the binder used, are between 50 and 450° C. The binders applied burn off within a short time after the introduction of the catalyst and startup of the reactor. The binder addition additionally has the advantage that the active composition adheres sufficiently on the support, so that transport and introduction of the catalyst are facilitated.

In a preferred embodiment of the process according to the invention with three catalyst layers, the catalysts have the following composition (the first layer being the layer arranged furthest upstream in flow direction of the gas stream):
for the first layer:
from 7 to 10% by weight of active composition based on the overall catalyst, this active composition comprising:
from 6 to 11% by weight of vanadium pentoxide
from 1.2 to 3% by weight of antimony trioxide
from 0.1 to 1% by weight of an alkali (calculated as alkali metal), especially cesium oxide, and, as the remainder to 100% by weight, titanium dioxide, preferably in anatase modification with a BET surface area of from 5 to 30 $m^2/g$
for the second layer:
from 7 to 12% by weight of active composition based on the overall catalyst, this active composition comprising:
from 5 to 13% by weight of vanadium pentoxide
from 0 to 3% by weight of antimony trioxide
from 0 to 0.4% by weight of an alkali (calculated as alkali metal), especially cesium oxide
from 0 to 0.4% by weight of phosphorus pentoxide (calculated as P),
and, as the remainder to 100% by weight, titanium dioxide, preferably in anatase modification with a BET surface area of from 10 to 40 $m^2/g$
for the third layer:
from 8 to 12% by weight of active composition based on the overall catalyst, this active composition comprising:
from 5 to 30% by weight of vanadium pentoxide
from 0 to 3% by weight of antimony trioxide
from 0 to 0.3% by weight of an alkali (calculated as alkali metal), especially cesium oxide
from 0.05 to 0.4% by weight of phosphorus pentoxide (calculated as P),
and, as the remainder to 100% by weight, titanium dioxide, preferably in anatase modification with a BET surface area of from 15 to 50 $m^2/g$.

The ratio of the volumes occupied by the first, second and third layer is preferably 100 to 200:40 to 100:40 to 100.

In a preferred embodiment of the process according to the invention with four catalyst layers, the catalysts have the following composition (the first layer being the layer arranged furthest upstream in flow direction of the gas stream):
for the first layer:
from 7 to 10% by weight of active composition based on the overall catalyst, this active composition comprising:
from 6 to 11% by weight of vanadium pentoxide
from 1.2 to 3% by weight of antimony trioxide
from 0.1 to 1% by weight of an alkali (calculated as alkali metal), especially cesium oxide, and, as the remainder to 100% by weight, titanium dioxide, preferably in anatase modification with a BET surface area of from 5 to 30 $m^2/g$
for the second layer:
from 7 to 10% by weight of active composition based on the overall catalyst, this active composition comprising:
from 4 to 15% by weight of vanadium pentoxide
from 0 to 3% by weight of antimony trioxide
from 0.1 to 1% by weight of an alkali (calculated as alkali metal), especially cesium oxide
from 0 to 0.4% by weight of phosphorus pentoxide (calculated as P),
and, as the remainder to 100% by weight, titanium dioxide, preferably in anatase modification with a BET surface area of from 10 to 35 $m^2/g$
for the third layer:
from 7 to 10% by weight of active composition based on the overall catalyst, this active composition comprising:
from 5 to 13% by weight of vanadium pentoxide
from 0 to 3% by weight of antimony trioxide
from 0 to 0.4% by weight of an alkali (calculated as alkali metal), especially cesium oxide
from 0 to 0.4% by weight of phosphorus pentoxide (calculated as P),
and, as the remainder to 100% by weight, titanium dioxide, preferably in anatase modification with a BET surface area of from 15 to 40 $m^2/g$
for the fourth layer:
from 8 to 12% by weight of active composition based on the overall catalyst, this active composition comprising:
from 10 to 30% by weight of vanadium pentoxide
from 0 to 3% by weight of antimony trioxide
from 0.05 to 0.4% by weight of phosphorus pentoxide (calculated as P),
and, as the remainder to 100% by weight, titanium dioxide, preferably in anatase modification with a BET surface area of from 15 to 50 $m^2/g$.

The ratio of the volumes occupied by the first, second, third and fourth layer is preferably 80 to 160:30 to 100:30 to 100:30 to 100.

If desired, a downstream finishing reactor can also be provided for phthalic anhydride preparation, as described, for example, in DE-A 198 07 018 or DE-A 20 05 969 A. The catalyst used is preferably an even more active catalyst compared to the catalyst of the last layer.

The catalysts are typically charged into reaction tubes which are thermostated externally to the reaction temperature, for example with a heat carrier medium, for example a salt melt. The gaseous stream is passed over the catalyst bed thus prepared at temperatures of generally from 300 to 450° C., preferably from 320 to 420° C. and more preferably from 340 to 400° C., and at an elevated pressure of generally from 0.1 to 2.5 bar, preferably from 0.3 to 1.5 bar, with a superficial velocity of generally from 750 to 5000 h$^{-1}$.

The reaction gas fed to the catalyst is generally obtained by mixing a gas which comprises molecular oxygen and, apart from oxygen, may also comprise suitable reaction moderators and/or diluents such as steam, carbon dioxide and/or nitrogen, with the aromatic hydrocarbon to be oxidized, and the molecular oxygen-comprising gas may comprise generally from 1 to 100 mol %, preferably from 2 to 50 mol % and more preferably from 10 to 30 mol % of oxygen, from 0 to 30 mol %, preferably from 0 to 10 mol % of steam, and from 0 to 50 mol %, preferably from 0 to 1 mol % of carbon dioxide, remainder nitrogen. To obtain the reaction gas, the molecular oxygen-comprising gas is charged generally at from 30 g to 150 g per m$^3$ (STP) of gas, preferably from 60 to 120 g per m$^3$ (STP), of the hydrocarbon to be oxidized.

It is possible for two or more zones, preferably two zones, of the catalyst bed present in the reaction tube to be thermostated to different reaction temperatures, for which, for example, reactors with separate salt baths can be used. Alternatively, the gas phase oxidation can also be performed at one reaction temperature without division in temperature zones.

The invention is illustrated in detail by the appended figure and the examples which follow.

EXAMPLES

Comparative Example 1

A commercial two-layer catalyst system which consisted of two catalysts of different activity was used. The upstream catalyst with lower activity is referred to as the selective catalyst, the downstream catalyst as the active catalyst. The active composition of both catalysts comprised titanium dioxide and vanadium oxide. The active composition was applied to steatite supports.

From the bottom upward, 130 cm of active catalyst and 170 cm of selective catalyst were introduced into a reactor consisting of an iron tube having a nominal width of 25 mm and a length of 360 cm. For temperature control, the iron tube was surrounded by a salt melt of a temperature of 350° C. 4 m$^3$ (STP) of air per tube were passed through the tube per hour from the top downward with loadings of 80 g of 98.5% strength by weight o-xylene/m$^3$ (STP) of air.

Figure 1:
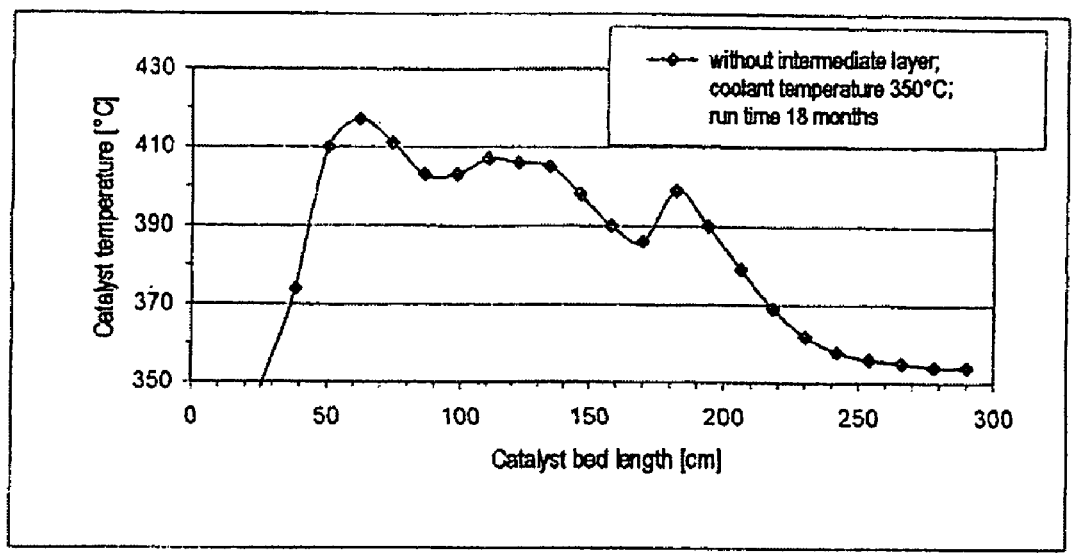
FIG. 1 shows the temperature profile of a two-layer catalyst system in the gas phase oxidation of o-xylene to phthalic anhydride (without moderator layer).

The temperature profile of this catalyst system after 18 months of operating time is shown in FIG. 1. It can be seen that the gaseous stream enters the layer of the active catalyst with a temperature of about 385° C. The yield after this operating time was 113.5 kg of phthalic anhydride per 100 kg of o-xylene used (based on pure o-xylene).

Example 2

Comparative Example 1 was repeated, except that the bed lengths of the catalyst system were modified in favor of a moderator layer. The moderator layer consisted of steatite rings (external diameter 7 mm, height 7 mm, internal diameter 4 mm). 125 cm of active catalyst, 15 cm of moderator layer and 170 cm of selective catalyst were introduced successively into the tubes.

Figure 2:
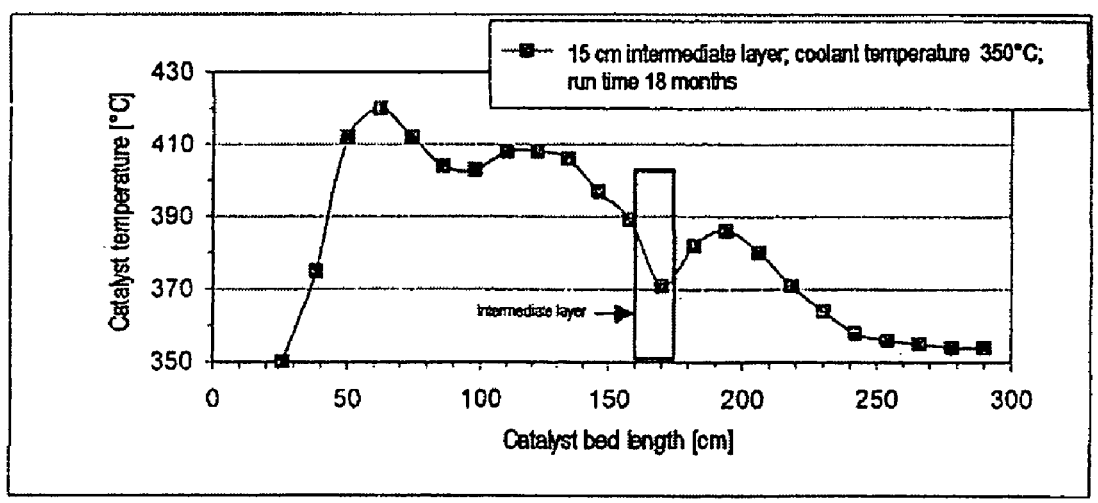
FIG. 2 shows the temperature profile of a two-layer catalyst system in the gas phase oxidation of o-xylene to phthalic anhydride with a catalytically inactive moderator layer between first and second catalyst layer.

The temperature profile of this catalyst system after 18 months of operating time at a salt bath temperature of 350° C. is shown in FIG. 2. It can be seen that the gaseous stream enters the layer of the active catalyst with a temperature of about 368° C., i.e. with a temperature about 17° C. lower compared to the Comparative Example. The yield after this operating time was 114.3 kg of phthalic anhydride per 100 kg of o-xylene used (based on pure o-xylene).

Comparative Example 3

The following catalysts 1 to 4 were used. The catalysts comprised shaped steatite bodies (magnesium silicate) in the form of rings (7×7×4 mm, ED×L×ID) with applied active composition.

Catalyst 1: active composition content: 8.0% of the total weight of the catalyst. Active composition (after calcination at 400° C. for 4 h): 7.1% by weight of $V_2O_5$, 1.8% by weight of $Sb_2O_3$, 0.36% by weight of Cs.

Catalyst 2: active composition content: 8.0% of the total weight of the catalyst. Active composition (after calcination at 400° C. for 4 h): 7.1% by weight of $V_2O_5$, 2.4% by weight of $Sb_2O_3$, 0.26% by weight of Cs.

Catalyst 3: active composition content: 8.0% of the total weight of the catalyst. Active composition (after calcination at 400° C. for 4 h): 7.1% by weight of $V_2O_5$, 2.4% by weight of $Sb_2O_3$, 0.10% by weight of Cs.

Catalyst 4: active composition content: 8.0% of the total weight of the catalyst. Active composition (after calcination at 400° C. for 4 h): 20.0% by weight of $V_2O_5$, 0.38% by weight of P.

The reactor used was a reactor consisting of an iron tube with an internal width of 25 mm and a length of 360 cm. The iron tube was surrounded by a salt melt for temperature control. Commencing with catalyst 4, the above catalysts were introduced so as to give rise to the following bed length distribution: 130/50/70/70 cm (catalyst 1/catalyst 2/catalyst 3/catalyst 4).

To operate the plant, an air/o-xylene mixture was passed through the main reactor from the top downward at a salt bath temperature of about 350° C.

Figure 3:
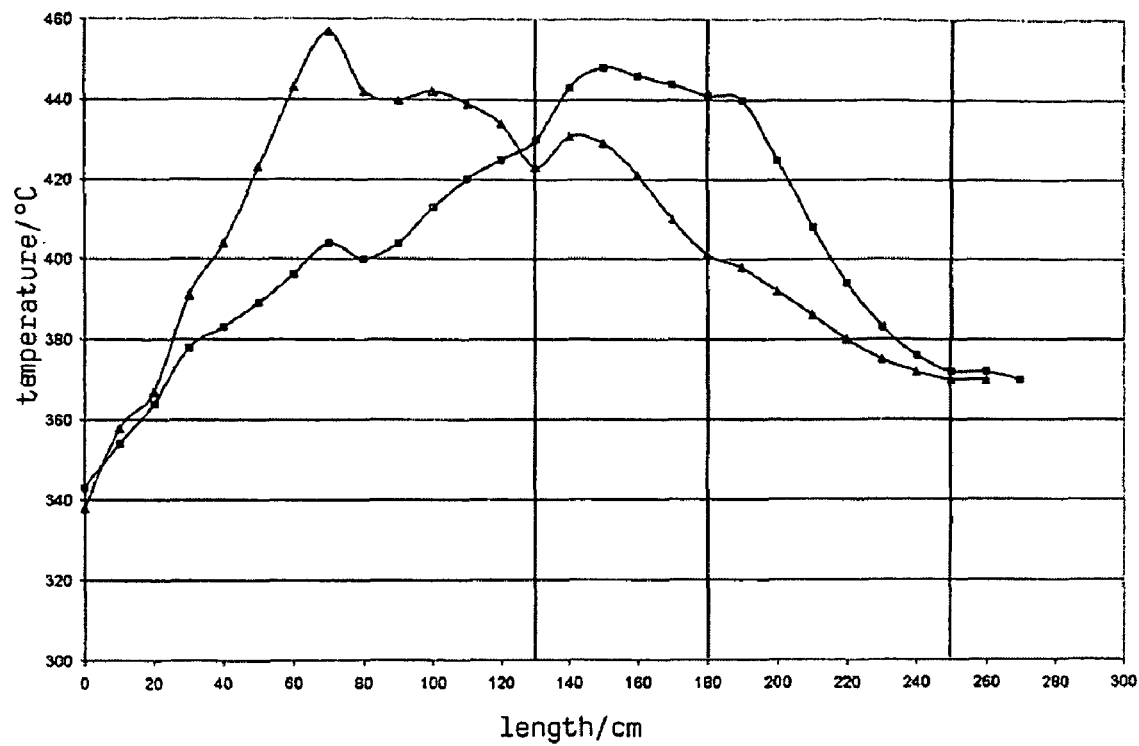
FIG. 3 shows the temperature profile of a four-layer catalyst system in the gas phase oxidation of o-xylene to phthalic anhydride (without moderator layer).

After a generally customary running-up time, the temperature profile specified in FIG. 3 (triangular symbols) was obtained. After a prolonged run time, the temperature profile characterized by the square symbols was obtained. It is seen that the hotspot profile shifts from the reactor inlet toward the reactor outlet with increasing run time. Immediately after the running-up, the entrance temperature into the third catalyst layer is about 400° C., but 440° C. after a prolonged run time. This leads to reduced selectivity and a falling overall yield.

Example 4

Comparative Example 3 was repeated, except that a catalytically inactive layer of steatite rings (external diameter 7 mm, height 7 mm, internal diameter 4 mm) was introduced as a moderator layer between the layer of catalyst 2 and of catalyst 3. The following bed length distribution was used: 130/70/10/55/55 cm (catalyst 1/catalyst 2/moderator layer/catalyst 3/catalyst 4).

Figure 4:
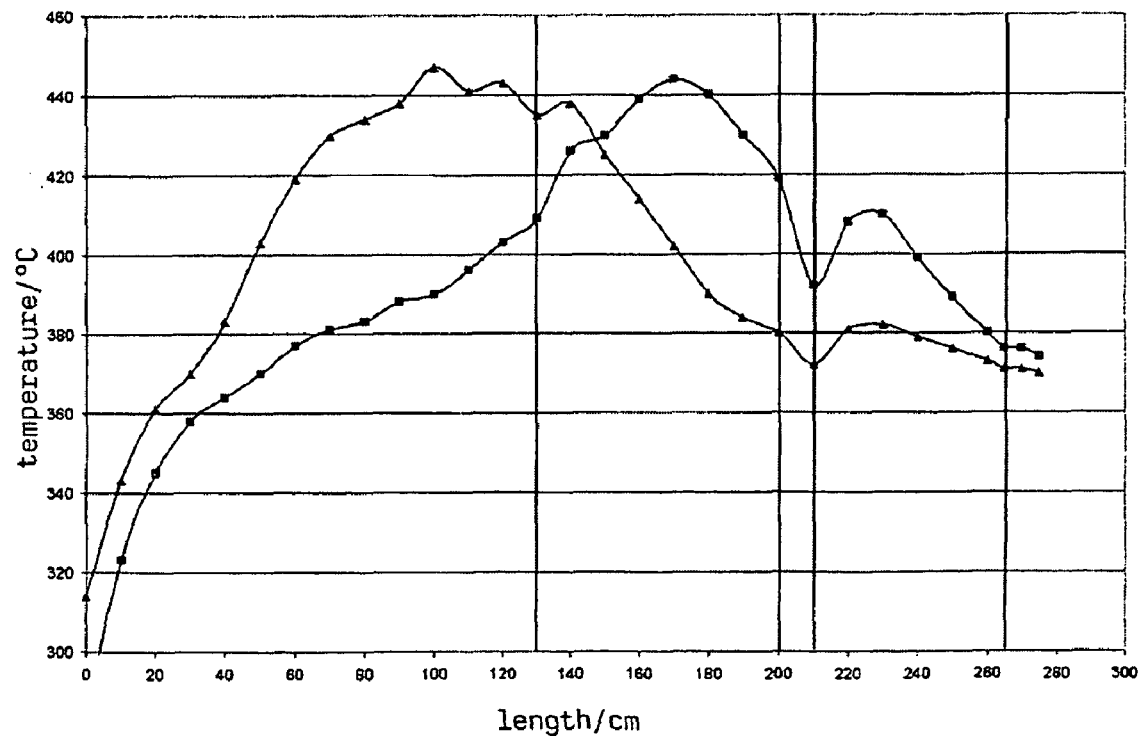
FIG. 4 shows the temperature profile of a four-layer catalyst system in the gas phase oxidation of o-xylene to phthalic anhydride with a catalytically inactive moderator layer between second and third catalyst layer.

After a generally customary running-up time, the temperature profile specified in FIG. 4 (triangular symbols) was obtained. After a prolonged run time, the temperature profile characterized by the square symbols was obtained. Immediately after the running-up, the cooling effect of the moderator layer is relatively minor. Once the hotspot profile has shifted with increasing run time, a significant cooling effect of the moderator layer is observed. As a result, the entrance temperature into the third catalyst layer falls. This promotes the selectivity of the reaction in the third catalyst layer.

The invention claimed is:

1. A process for gas phase oxidation in which a gaseous stream which comprises
    at least one aromatic hydrocarbon and molecular oxygen is passed through at least two catalyst layers arranged in succession in flow direction of the gaseous stream, the activity of the catalysts in adjacent catalyst layers being different from one another,
    wherein a moderator layer is arranged between two catalyst layers arranged in succession in flow direction of the gaseous stream, the moderator layer being less catalytically active than the catalysts adjacent upstream and downstream or being catalytically inactive and the catalyst layer downstream of the moderator layer has a higher activity than the catalyst layer upstream of the moderator layer and wherein the ratio of the volume of the moderator layer to the volume of the catalyst layer upstream of the moderator layer is from 0.02 to 0.35.

2. The process according to claim 1, wherein the gaseous stream is passed through at least three catalyst layers arranged in succession in flow direction of the gaseous stream.

3. The process according to claim 1, wherein the activity of the catalysts in flow direction of the gaseous stream increases constantly from one catalyst layer to the next from the catalyst layer closest to the gas inlet to the catalyst layer closest to the gas outlet.

4. The process according to claim 2, wherein the gaseous stream is passed through more than three catalyst layers arranged in succession in flow direction of the gaseous stream and the activity of the catalysts increases from one catalyst layer to the next over a sequence of at least three of the catalyst layers in flow direction of the gaseous stream.

5. The process according to claim 3, wherein a moderator layer is arranged at least upstream of the most active catalyst layer and/or second most active catalyst layer.

6. The process according to claim 1, wherein the temperature at the downstream border of the moderator layer is at least 2 K lower than $$(\delta T \cdot x)$$

wherein $\delta T$ is the gradient of the temperature profile at the border of the catalyst upstream of the moderator layer from the moderator layer, and x is the length of the moderator layer in flow direction.

7. The process according to claim 1, wherein the temperature drop over the moderator layer is at least 4 K.

8. The process according to claim 1, wherein the temperature of at least the moderator layer and the catalyst layers adjacent to it upstream and downstream can be controlled together.

9. The process according to claim 1, in which the catalytically active composition of all catalysts comprises at least vanadium oxide and titanium dioxide.

10. The process according to claim 1, in which the hydrocarbon used is o-xylene and/or naphthalene, and phthalic anhydride is prepared.

11. The process according to claim 2, wherein the activity of the catalysts in flow direction of the gaseous stream increases constantly from one catalyst layer to the next from the catalyst layer closest to the gas inlet to the catalyst layer closest to the gas outlet.

12. The process according to claim 4, wherein a moderator layer is arranged at least upstream of the most active catalyst layer and/or second most active catalyst layer.

13. The process according to claim 2, wherein the temperature at the downstream border of the moderator layer is at least 2 K lower than $$(\delta T \cdot x)$$

wherein $\delta T$ is the gradient of the temperature profile at the border of the catalyst upstream of the moderator layer from the moderator layer, and x is the length of the moderator layer in flow direction.

14. The process according to claim 3, wherein the temperature at the downstream border of the moderator layer is at least 2 K lower than $$(\delta T \cdot x)$$

wherein $\delta T$ is the gradient of the temperature profile at the border of the catalyst upstream of the moderator layer from the moderator layer, and x is the length of the moderator layer in flow direction.

15. The process according to claim 4, wherein the temperature at the downstream border of the moderator layer is at least 2 K lower than $$(\delta T \cdot x)$$

wherein $\delta T$ is the gradient of the temperature profile at the border of the catalyst upstream of the moderator layer from the moderator layer, and x is the length of the moderator layer in flow direction.

16. The process according to claim 5, wherein the temperature at the downstream border of the moderator layer is at least 2 K lower than $$(\delta T \cdot x)$$

wherein $\delta T$ is the gradient of the temperature profile at the border of the catalyst upstream of the moderator layer from the moderator layer, and x is the length of the moderator layer in flow direction.

17. The process according to claim 2, wherein the temperature drop over the moderator layer is at least 4 K.

18. The process according to claim 3, wherein the temperature drop over the moderator layer is at least 4 K.

19. The process according to claim 4, wherein the temperature drop over the moderator layer is at least 4 K.

20. The process according to claim 5, wherein the temperature drop over the moderator layer is at least 4 K.

* * * * *